United States Patent [19]

Neubert

[11] 4,244,361
[45] Jan. 13, 1981

[54] PORTABLE ELECTRICAL INHALATOR

[76] Inventor: Herbert O. Neubert, 231 Mabel Pl., Franklin Lakes, N.J. 07417

[21] Appl. No.: 29,803

[22] Filed: Apr. 13, 1979

[51] Int. Cl.³ .............................................. A61M 16/00
[52] U.S. Cl. ........................... 128/200.14; 128/200.21; 128/204.21; 128/205.25
[58] Field of Search ...................... 128/204.21, 200.14, 128/200.17, 205.18, 205.22, 205.25, 204.18, 203.29, 205.12, 203.12, 203.25, 203.28, 200.24, 203.13

[56] References Cited

U.S. PATENT DOCUMENTS

| 3,301,255 | 1/1967 | Thompson | 128/200.21 |
| 3,863,629 | 2/1975 | Ries | 128/205.12 |
| 4,076,021 | 2/1978 | Thompson | 128/205.18 |

FOREIGN PATENT DOCUMENTS

| 2635532 | 2/1977 | Fed. Rep. of Germany | 128/204.21 |
| 452964 | 11/1949 | Italy | 128/200.21 |

Primary Examiner—Henry J. Recla
Attorney, Agent, or Firm—Leo C. Krazinski

[57] ABSTRACT

A portable oral inhalator for use in a home, mobile vehicle and/or boat including a carrying case having compartments therein for compressor motor, dry cell batteries, switching controls, and medication. The inhalator provides optional control means therein for supplying 6 volt D.C. energy to the compressor motor, such as converting 110 volt A.C. power to 6 volt D.C. for home use, and 12 volt D.C. to 6 volt D.C. for vehicle or boat use, as well as a 6 volt D.C. dry battery source. The inhalator is useful in the treatment particularly for chronic asthmatics and other chronic pulmonary diseases.

6 Claims, 4 Drawing Figures

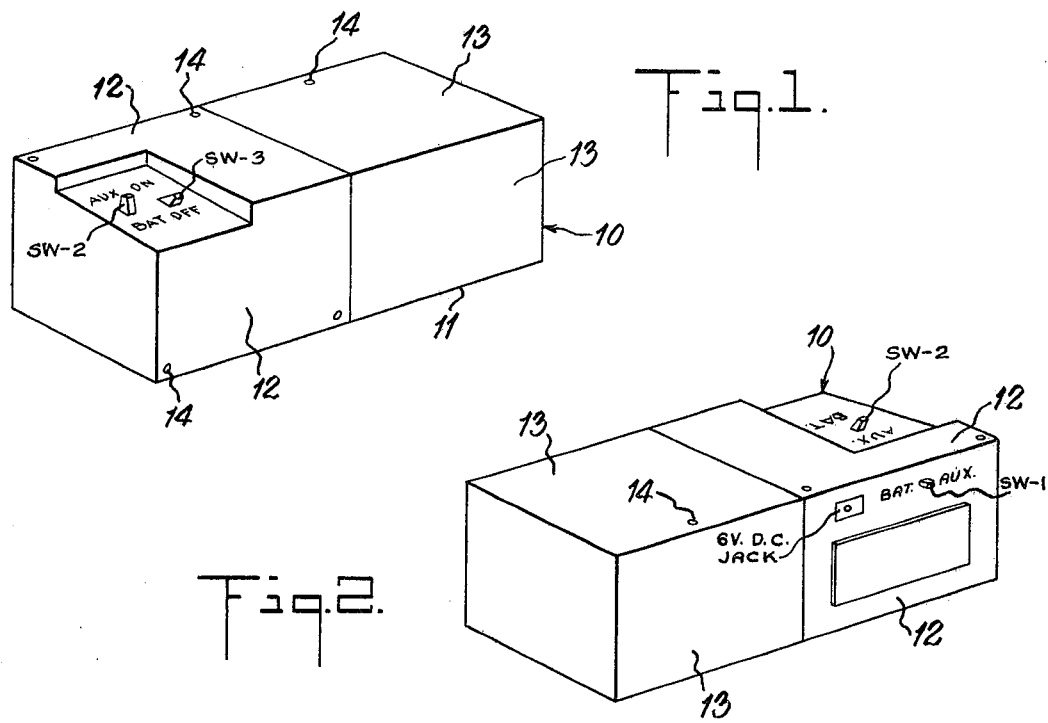
Fig. 1.
Fig. 2.
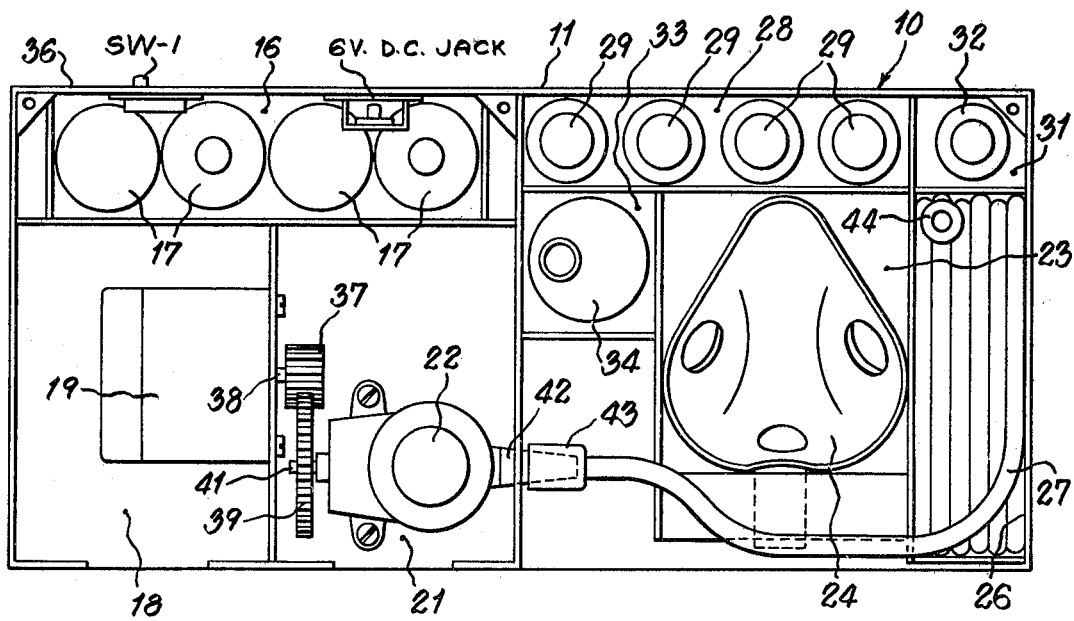
Fig. 3.

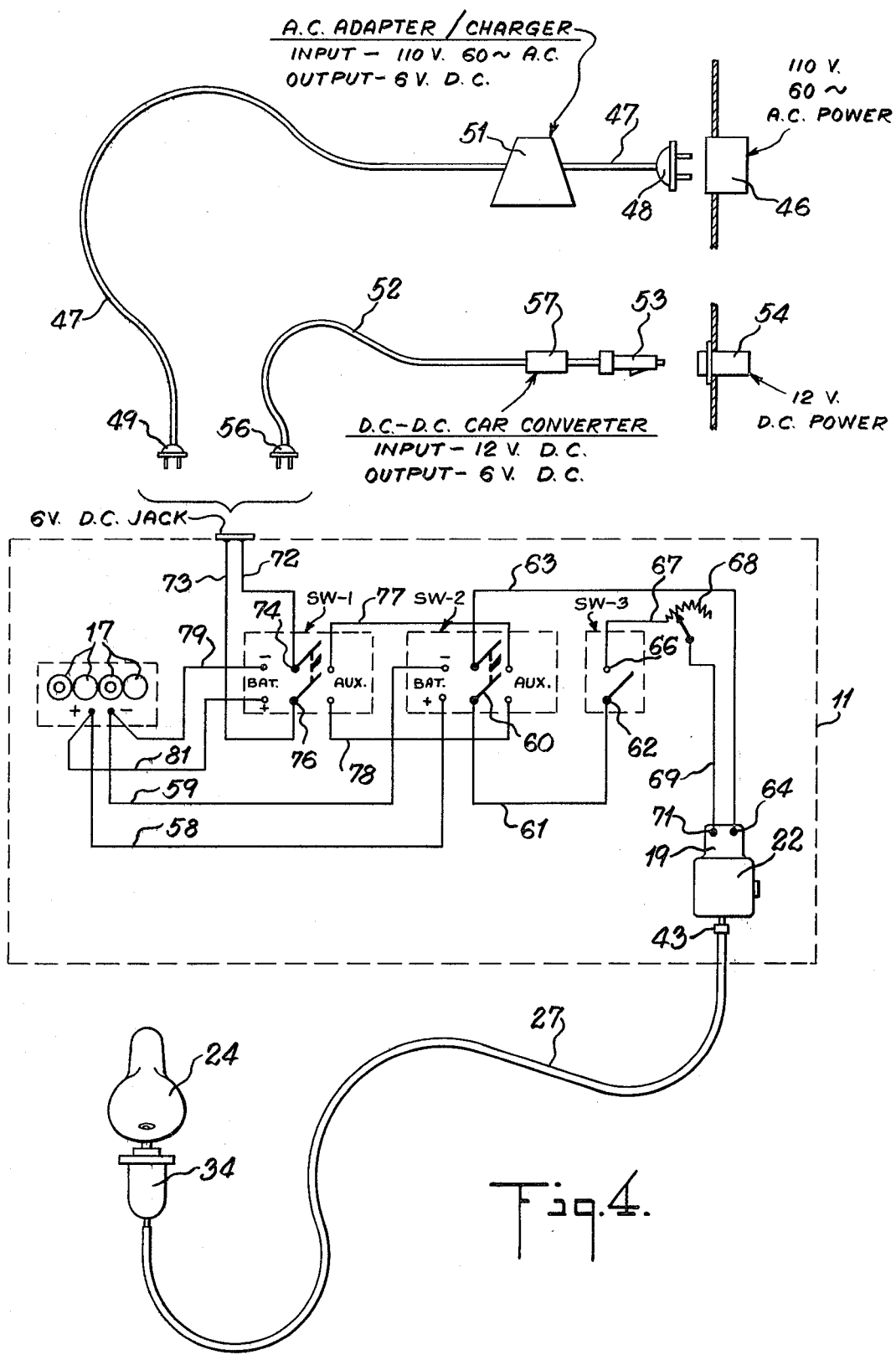

PORTABLE ELECTRICAL INHALATOR

BACKGROUND OF THE INVENTION

The present invention relates to electrically operated inhalators and, more particularly, to an electrically operated portable, self contained, inhalator which includes switching means for controlling optional sources of alternating or direct current to a 6 volt D.C. compressor motor. The portable inhalator can be operated at home, on a mobile vehicle or on a boat, utilizing the available sources of energy thereat.

DESCRIPTION OF PRIOR ART

Surgical inhalation apparatus are well known, as shown in U.S. Pat. Nos. 2,980,344, 3,581,742 and U.S. Pat. No. 4,026,285, but such apparatus are rather bulky and heavy in weight. As far as applicant is aware, there is no self contained, portable unit available for such inhalation apparatus.

SUMMARY OF THE INVENTION

Accordingly, an object of the present invention is to provide an improved portable inhalator that is comparatively light in weight.

Another object of the invention is to provide an improved portable inhalator that can be electrically energized by a variety of voltage sources.

A further object of the invention is to provide an improved portable inhalator that can be effectively used while on mobile vehicles, boats and all types of public transportation.

A still further object of the invention is to provide an improved portable inhalator that is simple, practical and economical in construction, and is reliable and efficient in operation.

Other and further objects will be obvious upon an understanding of the illustrative embodiment about to be described or will be indicated in the appended claims and various advantages not referred to herein will occur to one skilled in the art upon employment of the invention in practice.

BRIEF DESCRIPTION OF THE DRAWINGS

A preferred embodiment of the invention has been chosen for purposes of illustration and description and is shown in the accompanying drawings, forming a part of the specification, wherein:

FIG. 1 is a perspective view of a carrying case for an improved portable inhalator as shown from the front.

FIG. 2 is a perspective view of the portable inhalator of FIG. 1 but shown from the rear.

FIG. 3 is an enlarged top plan view of the portable inhalator with both covers removed so as to expose the interior with its component parts.

FIG. 4 is a schematic and wiring diagram of the portable inhalator showing choice of power supply and internal battery connections with switching controls.

DESCRIPTION OF PREFERRED EMBODIMENT

Referring now to the drawings, particularly to FIGS. 1, 2 and 3, there is shown a portable inhalator 10 having several compartments in a carrying case 11 for component parts thereof, as will be brought out hereinafter. The carrying case 11 in one instance has a height of 4½", a width of 5" and a length of 12". As seen in FIG. 1, a two-sided cover 12 encloses a left portion of the case 11 and a two-sided cover 13 encloses a right portion thereof, each cover being removably fastened by screws 14. In FIG. 3 are shown several compartments within the inhalator carrying case 11 including a compartment 16 for four "D" cell batteries 17, a compartment 18 for a motor 19, a compartment 21 for a compressor 22, a compartment 23 for a face mask 24, a compartment 26 for plastic tubing 27, a compartment 28 for medical supplies 29, a compartment 31 for a medicine dropper 32, and a compartment 33 for a nebulizer 34. In battery compartment 16 are mounted on wall 36 a control switch SW-1 and a 6 V DC JACK, as is also indicated in FIG. 2. In FIG. 1 are shown control switches SW-2 and SW-3, both mounted on upper cover 12. Referring again to FIG. 3, it is seen that the motor 19 is connected to the compressor 22 by a pinion 37 rigidly coupled to a shaft 38 on the motor 19 and in mesh engagement with a gear 39 rigidly coupled to a shaft 41 on the compressor 22. While not shown, the compressor 22 has a filtered air inlet, as is customary, and its outlet 42 is detachably connected to a coupling 43 at one end of the flexible plastic tubing 27, which at its other end 44 is adaptable for connection to the nebulizer 34 and in turn to the face mask 24, as will appear hereinafter.

Referring now to FIG. 4, there are shown three options for electrically energizing the inhalator 10. At the top of FIG. 4 is shown a conventional 110 volt A.C. power source outlet 46 to which is connectable a two conductor cord 47 having a plug 48 for connection to the A.C. outlet 46 at one end, a plug 49 at its other end for connection to the 6 volt D.C. JACK and an A.C. adapter/charger 51 intermediate the plugs 48,49. Below cord 47 is shown a two conductor cord 52 having at one end a plug 53 for connection to an outlet 54 of a conventional 12 volt D.C. source found in automobiles, boats, etc., at its other end a plug 56 for connection to the 6 volt D.C. JACK and a 12 V-6 V D.C. converter 57 intermediate the plugs 53,56. As is evident and since the motor 19 is operable by a 6 volt D.C. source, each of plugs 49 and 56 must likewise have 6 volt D.C. energy for insertion into the 6 volt D.C. JACK.

In operation, first let it be assumed that a patient wishes to use the portable inhalator 10 itself, relying on the batteries within the case 11 and without use of the cords 47 or 52. Accordingly, the circuit of FIG. 4 is set up by placing the proper medicine 29 in the nebulizer 34, connecting the face mask 24 to the output of the nebulizer 34, connecting the input of the nebulizer 34 to one end of the plastic tubing 27 and the other end of the plastic tubing 27 via coupling 43 to the output of the compressor 22, which is mechanically driven by the motor 19. Energy for driving the motor 19 may be traced from the battery 17 over leads 58, 59 to both BAT. terminals of the double-pole double-throw switch SW-2, arm 60 of which is thrown to the BAT. terminal position; thence via lead 61 to terminal 62 of open single-pole single-throw switch SW-3, and via lead 63 to terminal 64 of motor 19. Upon closure of switch SW-3 energy is then continued from its terminal 66 via lead 67, through rheostat 68 and over lead 69 to terminal 71 of motor 19. The motor 19 and compressor 22 being activated produce the required inhalation treatment in that filtered air is pumped through the compressor inlet port, through the flexible plastic tubing 27 to the nebulizer 34 containing the required medication, and then to the aerial face mask and patient. Upon completion of the treatment the single-pole single-throw switch SW-3 and the double-pole double-throw switch SW-2 are opened.

For use by a patient who is either at home, where 110 volt alternating current is available or in a vehicle or boat where 12 volt direct current is available, the patient uses cord 47 in the first instance and cord 52 in the second instance. The circuit operation is identical in either instance insofar as the motor operation is concerned. Assuming the patient is in a vehicle, the plug 53 of cord 52 is inserted into the cigar lighter outlet 54 and the plug 56 is inserted into the 6 V. D.C. JACK. The energy from the 6 V. D.C. JACK may be traced over leads 72 and 73 to terminals 74 and 76, respectively, of double-pole double-throw switch SW-1, which is closed to AUX terminals, the energy then passing over leads 77,78 to AUX terminals of double-pole double-throw switch SW-2. Upon closing arm 60 of the switch SW-2 to the AUX terminals the energy will flow to the motor 19 in the same manner as described heretofore with respect to the battery 17 source, and need not be repeated.

In the event rechargeable batteries 17 are provided for the inhalator 10, these batteries may be charged by use of cord 47 that is energized by plugging the input plug 48 into 110 volt A.C. power source outlet 46 and the output plug 49 into the 6 V. D.C. JACK, and then closing the double-pole double-throw switch SW-1 to its BAT. terminals. Six volt energy thus passes from the 6 V. D.C. JACK along leads 72 and 73 onto SW-1 switch terminals 74 and 76, respectively, through its BAT terminals and leads 79 and 81 to the batteries 17. The batteries are charged for the required period to bring them up to the required charge.

From the foregoing description, it will be seen that the present invention provides a portable inhalator that is of great help to persons suffering from chronic asthmatics and pulmonary diseases particularly at times when they might be travelling and away from home, where stationary inhalator devices are available.

As various changes may be made in the form, construction and arrangement of the parts herein, without departing from the spirit and scope of the invention and without sacrificing any of its advantages, it is to be understood that all matters are to be interpreted as illustrative and not in any limiting sense.

What is claimed is:

1. A portable oral inhalator for supplying medicament to the respiratory system of a human body comprising, in combination, a carrying case, a plurality of compartments in said carrying case for segregated component parts in individual compartments thereof including a motor, a compressor, means interconnecting said motor and said compressor, a nebulizer, plastic tubing for interconnecting said compressor and one side of said nebulizer, a face mask connectable to the other side of said nebulizer, and medicine for placement in said nebulizer, whereby air produced by said compressor and fed into said medically treated nebulizer supplies medicated air through said face mask and upon a patient's face, means including a plurality of electrical power sources, electrical control means connectable to said power sources for supplying energy to said motor said plurality of electric power sources include dry cell batteries having a voltage of 6 volts disposed in a first one of said compartments, a first cord having an input plug at one end, an output plug at the other end thereof and an A.C. adapter charger intermediate the plugs in which the input plug is adaptable for insertion into a 110 volt A.C. socket and the output plug is adaptable for insertion into a 6 volt D.C. jack; and a second cord having an input plug at one end, an output plug at the other end thereof, and a 12 volt D.C.–6 volt D.C. converter intermediate the plugs in which the input plug is adaptable for insertion into a 12 volt D.C. socket and the output plug is adaptable for insertion into a 6 volt D.C. jack, and wherein said motor is disposed in a second one of said compartments, said compressor is in a third compartment, gear means in said third compartment for interconnecting said compressor and motor, said nebulizer is in a fourth compartment, plastic tubing is in a fifth compartment having one end connectable to said compressor and its other end connectable to said nebulizer, and said face mask is in a sixth compartment being connectable to said nebulizer.

2. A portable oral inhalator in accordance with claim 1, wherein said control means for a self-contained battery supply include an open first double-pole double-throw switch, an open single-pole single-throw switch, a rheostat, said double-pole double-throw switch having a pair of terminals connected to said batteries, a terminal on an arm of said double-pole double-throw switch connected to one terminal of said motor, another spaced terminal on the arm thereof connected to a terminal on one side of said single-pole single-throw switch, a terminal on the other side of said single-pole single-throw switch connected to an input terminal of said rheostate, and a terminal on the output side of said rheostat connected to another terminal of said motor, whereby upon closure of said two switches into engagement with said terminals 6 volt D.C. power energizes said motor and in turn operates said compressor.

3. A portable oral inhalator in accordance with claim 1, wherein said control means for a self-contained battery supply charging circuit include an open double-pole double-throw switch, a 6 volt D.C. jack, a second cord having its input plug inserted into a 12 volt D.C. socket of a vehicular power source and its output plug inserted into said jack, and said double-pole double-throw switch having a pair of terminals connected to said batteries and a pair of terminals on an arm thereof connected to said jack, whereby upon closure of said double-pole double-throw switch into engagement with said battery connected terminals 6 volt D.C. power is impressed upon said batteries to charge the same.

4. A portable oral inhalator in accordance with claim 1, wherein said control means for a vehicular 12 volt D.C. or a 110 A.C. supply source include an open first double-pole double-throw switch, an open second double-pole double-throw switch, a D.C. jack having 6 volt D.C. energy connected thereto, an open single-pole single-throw switch, a rheostat, said first double-pole double-throw switch having a pair of terminals, a terminal on an arm thereof connected to one terminal of said motor, another terminal on the arm thereof connected to a terminal on one side of said single-pole single-throw switch, a terminal on the other side of said single-pole single-throw switch connected to an input terminal of said rheostat, an output side of said rheostat connected to another terminal of said motor, said second double-pole double-throw switch having a pair of terminals connected to said pair of terminals of said first double-pole double-throw switch, and a pair of terminals on an arm of said second double-pole double-throw switch connected to said jack, whereby upon closure of said three switches into engagement with said terminals 6 volt D.C. power energizes said motor and in turn operates said compressor.

5. A portable oral inhalator in accordance with claim 4, wherein said 6 volt D.C. energy at said jack includes a first cord having its input plug inserted into a 110 volt A.C. socket of a power source and its output plug inserted into said jack.

6. A portable oral inhalator in accordance with claim 4, wherein said 6 volt D.C. energy at said jack includes a second cord having its input plug inserted into a 12 volt D.C. socket of a vehicular power source and its output plug inserted into said jack.

* * * * *